United States Patent [19]

Haber

[11] Patent Number: 4,500,520

[45] Date of Patent: * Feb. 19, 1985

[54] ANTIINFLAMMATORY AND/OR ANALGESIC SILYLFURANS

[75] Inventor: Stephen B. Haber, Wilmington, Del.

[73] Assignee: E. I. Du Pont de Nemours and Company, Wilmington, Del.

[*] Notice: The portion of the term of this patent subsequent to Feb. 21, 2001 has been disclaimed.

[21] Appl. No.: 471,201

[22] Filed: Mar. 1, 1983

[51] Int. Cl.$^3$ .................. A61K 31/725; C07F 7/18
[52] U.S. Cl. ................................ 514/63; 549/214; 546/14
[58] Field of Search .............. 549/214; 424/184; 546/14

[56] References Cited

U.S. PATENT DOCUMENTS

| | | | |
|---|---|---|---|
| 2,639,286 | 5/1953 | Mavity | 260/329 |
| 3,692,798 | 9/1972 | Barcza | 424/184 |
| 3,745,215 | 7/1973 | Kaugars | 424/327 |
| 3,870,505 | 3/1975 | Kaugars | 71/121 |
| 4,432,974 | 2/1984 | Haber | 424/184 |

OTHER PUBLICATIONS

Tanikaga et al., J. Chem. Soc. Chem. Comm., 1106 (1981).
Mandai et al., Tet. Lett., 22, 2187 (1981).
Garst et al., J. Org. Chem., 39, 584 (1974).
Hendrickson et al., J. Am. Chem. Soc., 86, 107 (1964).
Lukerics et al., Khim. Geterotsikl. Soedn., Akad. Nuak Latv. SSR, 1965 (1) 31-35.
Eaborn et al., J. Chem. Soc., 1961, 4921-4927.
Benkeser et al., J. Am. Chem. Soc., 70, 1780-1782 (1948).
Lapkin et al., Khim.-Farm. Zhur., 15 (5), 39-44 (May 1981) (Transl. pp. 319-323).
Lukevits et al., Khim.-Farm. Zhur., 15 (4), 42-46 (1981).
R. A. Scherrer et al., Antiinflammatory Agents Chemistry and Pharmacology, vol. 1, p. 29 (1974).
Gund et al., J. Med. Chem., vol. 20, No. 9, p. 1146 (1977).
Appleton et al., Prostaglandins, vol. 18, No. 1, p. 29 (1979).
Schatz, Burger Medicinal Chemistry, 2nd Ed., p. 72 (1960).

Primary Examiner—Nicky Chan

[57] ABSTRACT

Silyldiarylfurans, such as 4,5-bis(4-methoxyphenyl)-2-trimethylsilylfuran, are useful in the treatment of inflammation and/or pain.

8 Claims, No Drawings

ANTIINFLAMMATORY AND/OR ANALGESIC SILYLFURANS

BACKGROUND OF THE INVENTION

1. Field of the Invention

This invention relates to silyldiarylfurans, pharmaceutical compositions containing them and methods of using them to treat inflammation and/or pain in mammals.

2. Prior Art

There is a continuing need for safe and effective antiinflammatory agents to treat inflammation, a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment as well.

The usefulness of many commercial antiinflammatories, however, is limited because of toxicity and adverse side-effects. Many produce gastric irritation and can cause changes in blood cells or can affect the central nervous system. Adreno-cortical steroids, for example, produce gastric irritation and suppression of normal adrenal function.

The present invention results from efforts to develop new anti-arthritic compounds with good antiinflammatory activity and minimal side effects that could be more effective in treating arthritis than are presently available drugs. In addition to antiinflammatory properties, some compounds of this invention have demonstrated analgesic activity in a test procedure. This additional property is desirable in treatment of arthritis or related diseases; however, such compounds can be employed solely to alleviate pain.

2-Furylsilanes are known in the literature [e.g., E. Lukerics and M. G. Voronkov, *Khim. Geterotsikl. Soedn., Akad. Nauk Latv. SSR*, 1965 (1), 31–5 (CA 63:2994d) (1965). See also C. Eaborn and J. S. Sperry, *J. Chem. Soc.*, 1961, 4921–7; R. A. Benkeser and R. B. Currie, *J. Am. Chem. Soc.*, 70, 1780–2 (1948).] None are known where aromatic substituents are present in the furan ring.

Silyldiarylthiophenes, such as 4,5-bis(4-methoxyphenyl)-2-trimethylsilylthiophene, are claimed as antiinflammatories and/or analgesics in coassigned U.S. application Ser. No. 354,643, filed Mar. 4, 1982, now U.S. Pat. No. 4,432,974.

SUMMARY OF THE INVENTION

According to the present invention there is provided a compound having the formula I:

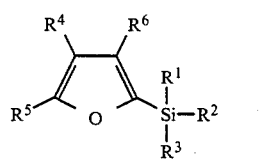
(I)

wherein $R^1$, $R^2$ and $R^3$ are independently H, alkoxy of 1–2 carbon atoms, alkyl of 1–7 carbon atoms optionally substituted with halogen, preferably fluorine, alkenyl of 2–7 carbon atoms, phenyl or benzyl, with the proviso that the sum of the number of carbon atoms in $R^1$, $R^2$ and $R^3$ must be at least 1 and not greater than 9 with the additional proviso that no more than 2 of $R^1$, $R^2$ and $R^3$ are alkoxy;

$R^4$ and $R^5$ are independently pyridyl or

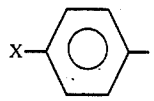

where X is H, F, Cl, Br, $R^7$, $OR^7$, $S(O)_nR^7$, $NO_2$, or

where n=0, 1 or 2; $R^7$=alkyl of 1–2 carbon atoms and $R^8$=alkyl of 1–2 carbon atoms;

with the proviso that $R^4$ and $R^5$ cannot both be

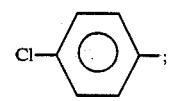

and $R^6$ is H, or alkyl of 1–2 carbon atoms; or a pharmaceutically suitable salt thereof.

Also provided are pharmaceutical compositions containing at least one of the aforesaid compounds and methods of using them to treat inflammation and/or pain in mammals.

PREFERRED SCOPE

Compounds of preferred scope are those of the formula:

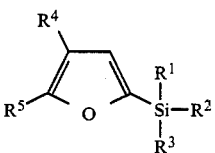
(Ia)

where $R^4$ and $R^5$ are independently

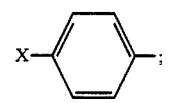

where X is H, $OR^7$, F, or $R^7$;

$R^1$, $R^2$ and $R^3$ are independently H, alkoxy of 1–2 carbon atoms, alkyl of 1–7 carbon atoms optionally substituted with halogen, preferably fluorine, alkenyl of 2–7 carbon atoms, phenyl or benzyl, with the proviso that the sum of the number of carbon atoms in $R^1$, $R^2$ and $R^3$ must be at least 1 and not greater than 9 with the additional proviso that no more than 2 of $R^1$, $R^2$ and $R^3$ are alkoxy.

More preferred compounds are compounds of Formula Ia where:

$R^4$ and $R^5$ are independently

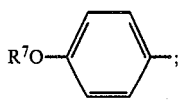

where
R[7] is alkyl of 1–2 carbon atoms.

Most preferred compounds are compounds of Formula Ia where:

R[4] and R[5] are independently

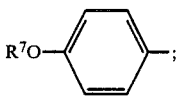

where

R[7] is alkyl of 1–2 carbon atoms; and

R[1], R[2] and R[3] are independently H, alkyl of 1–3 carbon atoms, or alkenyl of 2–3 carbon atoms with the proviso that the sum of the number of carbon atoms in R[1], R[2] and R[3] must be at least 2 and not greater than 5.

Specifically preferred because of its biological activity is 4,5-bis(4-methoxyphenyl)-2-trimethylsilylfuran:

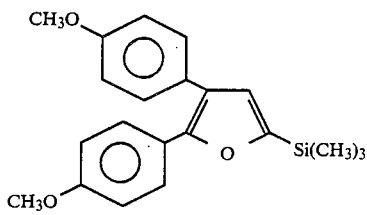

This invention includes pharmaceutically suitable salts of the above compounds in which at least one of R[4] and R[5] is pyridyl or di(C$_{1-2}$ alkyl)aminophenyl. Such salts, the preparation of which is well known to those skilled in pharmaceuticals, include acid addition salts with acids such as hydrochloric, sulfuric, and nitric acids.

Compounds of the invention in which no two of R[1], R[2], and R[3] are the same or in which at least one of R[4] and R[5] is 4-methylsulfinylphenyl exist as mixtures of enantiomers or diastereoisomers. This invention includes such mixtures as well as preparations enriched in, or consisting substantially of, one or more of the component isomers.

SYNTHESIS

The compounds (I) of this invention are prepared from 2,3-diarylfurans II. The latter are prepared using methods described in the literature: [R. Tanikaga, et al., *J. Chem. Soc. Chem. Commun.*, 1106 (1981); T. Mandai, et al., *Tet. Lett.*, 22, 2187 (1981); M. E. Garst and T. A. Spencer, *J. Org. Chem.*, 39, 584 (1974); and J. B. Hendrickson, et al., *J. Am. Chem. Soc.*, 86, 107 (1964)]. Several methods can be used.

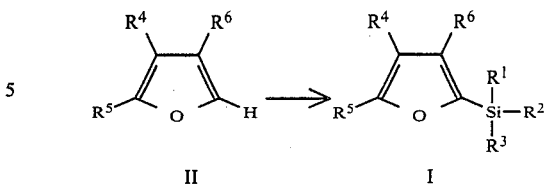

Method A

A 2,3-diarylfuran II is treated with a strong base such as n-butyl lithium or t-butyl lithium in an aprotic solvent such as diethyl ether, dimethoxyethane, tetrahydrofuran, or toluene, optionally in the presence of a complexing agent such as tetramethylethylenediamine, and then treated with a R[1]R[2]R[3] silyl halide such as trimethylsilyl chloride to give a compound of Formula I. The reaction can be carried out at temperatures from $-78°$ C. to the reflux temperature of the solvent used.

Method B

A 2,3-diarylfuran II is treated with a strong base such as n-butyl lithium or t-butyl lithium in an aprotic solvent such as diethyl ether, dimethoxyethane, tetrahydrofuran, or toluene, and then treated with a R[1]R[2] silyl dichloride. The resulting intermediate is then treated with a reducing agent such as lithium aluminum hydride or di-isobutyl aluminum hydride to give a compound of Formula I. If one of R[1] and R[2] in the silyl dichloride is H, then compounds I in which two of R[1], R[2], and R[3] are H are obtained.

Method C

Compounds I of this invention where R[1], R[2], or R[3] is alkoxy may be prepared by reacting a 2,3-diarylfuran II with a strong base such as n-butyl lithium or t-butyl lithium in an aprotic solvent such as diethyl ether, dimethoxyethane, tetrahydrofuran, or toluene, and then reacting the metallated furan with a R[1]R[2] silyl dichloride. The resulting intermediate is reacted with an alcohol such as methanol or ethanol to give a compound of Formula I. If one of R[1] and R[2] in the silyl dichloride is alkoxy, compounds I in which two of R[1], R[2], and R[3] are alkoxy are obtained.

The compounds of this invention and their synthesis are further illustrated by the following examples. All temperatures are in degrees centigrade. The following abbreviations are used: IR-infrared, PMR-proton nuclear magnetic resonance, MS-mass spectrum.

EXAMPLE 1

4,5-bis(4-Fluorophenyl)-2-trimethylsilylfuran

A solution of 2,3-bis(4-fluorophenyl)furan (7.0 g, 27 mmoles) in 100 ml of dry dimethoxyethane was cooled to $-35°$ and treated dropwise with n-butyl lithium (1.6M; 18.8 ml, 30 mmoles). The solution was stirred at $-35°$ for one hour and treated with chlorotrimethylsilane (3.0 g, 27.6 mmoles). The reaction mixture was stirred at $-35°$ for one hour and at room temperature for 24 hours. The mixture was concentrated in vacuo, suspended in 180 ml of carbon tetrachloride, and filtered through 50 g of silica gel. The filtrate was concentrated to an oil which crystallized on standing to yield 8.1 g (90%) of the title compound, m.p. 82°–83°. PMR (CDCl$_3$) δ0.33 (s, 9H, Si(CH$_3$)$_3$); 6.87 (s, 1H, H—C= C—O), 6.9–7.8 (m, 8H, 2-p-FC$_6$H$_4$). MS: m/z 328.

Anal. Calcd. for C$_{19}$H$_{18}$F$_2$OSi: C, 69.5; H, 5.5. Found: C. 70.0, H, 5.6.

EXAMPLE 2

4,5-bis(4-Methoxyphenyl)-2-trimethylsilylfuran

By substituting 2,3-bis(4-methoxyphenyl)furan in the procedure of Example 1, the title compound was obtained as an oil in 83% yield. PMR (CDCl$_3$): δ0.37 (s, 9H, Si(CH$_3$)$_3$); 3.80 (s, 3H, OCH$_3$); 3.83 (s, 3H, OCH$_3$); 6.85 (s, 1H, H—C=C—O); 6.8–7.2 (m, 4H, 4-MeOC$_6$H$_4$; 7.3–7.8 (m, 4H, 4-MeOC$_6$H$_4$. MS: m/z 352.

EXAMPLE 3

4,5-Diphenyl-2-trimethylsilylfuran

By substituting 2,3-diphenylfuran in the procedure of Example 1, the title compound was obtained as an oil in 100% yield. PMR (CCl$_4$): δ0.28 (s, 9H, SiMe$_3$); 6.70 (s, 1H, H—C=C—O); 6.9–7.7 (m, 10H, 2-C$_6$H$_4$). MS: m/z 292.

EXAMPLE 4

5-(4-Fluorophenyl)-4-(4-methylthiophenyl)-2-trimethylsilylfuran

By substituting 2-(4-fluorophenyl)-3-(4-methylthiophenyl)furan in the procedure of Example 1, the title compound was obtained as an oil in 99% yield. PMR (CCl$_4$): δ3.0 (s, 9H, SiMe$_3$); 2.37 (s, 3H, SCH$_3$); 6.60 (s, 1H, H—C=C—O); 6.7–7.6 (m, 8H, 2-Ar). MS: m/z 356.

EXAMPLE 5

5-(4-Chlorophenyl)-4-(4-methylphenyl)-2-trimethylsilylfuran

By substituting 2-(4-chlorophenyl)-5-(4-tolyl)furan in the procedure of Example 1, the title compound was obtained in 88% yield, m.p. 80°–84°. PMR (CDCl$_3$): δ0.40 (s, 9H, SiMe$_3$); 2.43 (s, 3H, MeC$_6$H$_4$); 6.88 (s, 1H, H—C=C—O); 7.1–7.8 (m, 8H, 2-Ar). MS: m/z 340.

The compounds of Examples 1–5 and other compounds which can be made by the procedures described are listed in Table I.

TABLE I

| Ex. | R$^1$ | R$^2$ | R$^3$ | R$^4$ | R$^5$ | R$^6$ |
|---|---|---|---|---|---|---|
| 1 | Me | Me | Me | 4-FC$_6$H$_4$ | 4-FC$_6$H$_4$ | H |
| 2 | Me | Me | Me | 4-MeOC$_6$H$_4$ | 4-MeOC$_6$H$_4$ | H |
| 3 | Me | Me | Me | C$_6$H$_5$ | C$_6$H$_5$ | H |
| 4 | Me | Me | Me | 4-MeSC$_6$H$_4$ | 4-FC$_6$H$_4$ | H |
| 5 | Me | Me | Me | 4-MeC$_6$H$_4$ | 4-ClC$_6$H$_4$ | H |
| 6 | Me | Me | Me | 4-BrC$_6$H$_4$ | 4-BrC$_6$H$_4$ | H |
| 7 | Me | Me | Me | 4-MeSOC$_6$H$_4$ | 4-FC$_6$H$_4$ | H |
| 8 | Me | Me | Me | 4-MeSO$_2$C$_6$H$_4$ | 4-FC$_6$H$_4$ | H |
| 9 | Me | Me | Me | 4-FC$_6$H$_4$ | 4-MeSC$_6$H$_4$ | H |
| 10 | Me | Me | Me | 4-FC$_6$H$_4$ | 4-MeS(O)C$_6$H$_4$ | H |
| 11 | Me | Me | Me | 4-FC$_6$H$_4$ | 4-MeSO$_2$C$_6$H$_4$ | H |
| 12 | Me | Me | Me | 2-pyridyl | 2-pyridyl | H |
| 13 | Me | Me | Me | 4-Me$_2$NC$_6$H$_4$ | 4-Me$_2$NC$_6$H$_4$ | H |
| 14 | Me | Me | Me | 4-EtOC$_6$H$_4$ | 4-EtOC$_6$H$_4$ | H |
| 15 | Me | Me | Me | 4-NO$_2$C$_6$H$_4$ | 4-NO$_2$C$_6$H$_4$ | H |
| 16 | Me | Me | CH=CH$_2$ | 4-MeOC$_6$H$_4$ | 4-MeOC$_6$H$_4$ | H |
| 17 | Me | Me | CH$_2$—CH=CH$_2$ | 4-MeOC$_6$H$_4$ | 4-MeOC$_6$H$_4$ | H |
| 18 | Me | Me | CH$_2$CH$_2$CH$_3$ | 4-MeOC$_6$H$_4$ | 4-MeOC$_6$H$_4$ | H |
| 19 | Et | Et | Et | 4-MeOC$_6$H$_4$ | 4-MeOC$_6$H$_4$ | H |
| 20 | Me | Me | t-Bu | 4-MeOC$_6$H$_4$ | 4-MeOC$_6$H$_4$ | H |
| 21 | Me | Me | C$_6$H$_5$ | 4-MeOC$_6$H$_4$ | 4-MeOC$_6$H$_4$ | H |
| 22 | Me | Me | CH$_2$Ph | 4-MeOC$_6$H$_4$ | 4-MeOC$_6$H$_4$ | H |
| 23 | Me | H | H | 4-MeOC$_6$H$_4$ | 4-MeOC$_6$H$_4$ | H |
| 24 | Me | Me | Me | 4-MeOC$_6$H$_4$ | 4-MeOC$_6$H$_4$ | Me |
| 25 | Me | Me | OMe | 4-MeOC$_6$H$_4$ | 4-MeOC$_6$H$_4$ | H |
| 26 | Me | Me | Me | 3-pyridyl | 3-pyridyl | H |
| 27 | Me | Me | Me | 4-pyridyl | 4-pyridyl | H |
| 28 | Me | OMe | OMe | 4-MeOC$_6$H$_4$ | 4-Et$_2$NC$_6$H$_4$ | H |
| 29 | Me | Me | OEt | 4-MeOC$_6$H$_4$ | 4-MeOC$_6$H$_4$ | H |
| 30 | Me | Me | CH$_2$CH$_2$CF$_3$ | 4-MeOC$_6$H$_4$ | 4-MeOC$_6$H$_4$ | H |
| 31 | Me | Me | n-C$_7$H$_{15}$ | 4-MeOC$_6$H$_4$ | 4-MeOC$_6$H$_4$ | H |
| 32 | Me | Me | (CH$_2$)$_5$CH=CH$_2$ | 4-MeOC$_6$H$_4$ | 4-MeOC$_6$H$_4$ | H |

Me = CH$_3$
Et = C$_2$H$_5$
Bu = C$_4$H$_9$

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Some of the compounds of this invention form salts. Solutions for parenteral administration of these compounds contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

SOFT GELATIN CAPSULES

A mixture of active ingredient in soybean oil is prepared and injected by means of a positive displacement pump into gelatin to form soft gelatin capsules containing 75 milligrams of the active ingredient. The capsules are washed and dried.

TABLETS

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by dissolving 1% by weight of active ingredient in sodium chloride injection U.S.P. $\times \times$ and adjusting the pH of the solution to between 6 and 7. The solution is sterilized by commonly used techniques.

USE

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, 32, (2)(1973) "Models Used for the Study and Therapy of Rheumatoid Arthritis"—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

ESTABLISHED ADJUVANT-INDUCED ARTHRITIS IN RATS

Male Charles River Lewis rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control}}{\text{Mean Paw Volume (ml)}} - \frac{\text{Treatment Group}}{\text{Mean Paw Volume (ml)}} \times 100 =$$
$$\frac{\text{Arthritic Control}}{\text{Mean Paw Volume (ml)}} - \frac{\text{Non-Arthritic Control}}{\text{Mean Paw Volume (ml)}}$$

% Decrease from Control Mean Paw Volume.

Dose-response regression lines of the percent decrease are plotted on semi-log paper by visual fit and the effective dose for 50% decrease from control paw volume (ED50) is determined by inspection. Data for some of the compounds of this invention are summarized in Table II.

Compounds from this series were also compared to indomethacin, phenylbutazone, ibuprofen, and aspirin.

PHENYLQUINONE WRITHING TEST

A standard procedure for detecting and comparing the analgesic activity of compounds in this series for which there is a good correlation with human efficacy is the standard phenylquinone writhing test modified from Siegmund, et al., Proc. Soc. Exp. Biol. Med., 95, 729 (1957). A test compound suspended in 1% methylcellulose was given orally to fasted (17-21 hours) female white mice, 5-20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., Bact. Rev., 11, 115-145 (1947); the time of peak activity was determined for many of the compounds. Data for some of the compounds are summarized in Table II together with data for some standard analgetic-antiinflammatory drugs.

TABLE II

| Example | Biological Activity | |
|---|---|---|
| | Adjuvant Arthritis $ED_{50}$ (mg/kg) | Phenylquinone Writhing (PQW) $ED_{50}$ (mg/kg) |
| 1 | (32% at 27)[1] | 39 |
| 2 | 2.5 | 2.3 |
| 3 | (24% at 27)[1] | 94 |
| 4 | >27[2] | >135 |
| 5 | (15% at 27)[2] | >135 |
| Indomethacin | 0.3 | 0.35 |
| Phenylbutazone | 10 | 80 |
| Ibuprofen | 100 | 10 |
| Aspirin | 305 | 135 |

[1] Values in parentheses indicate the percent reduction in paw volume at the indicated dose.
[2] Tested at 27 mg/kg; formulations were judged not to be satisfactory; compound may be active at 27 mg/kg or less if formulations were satisfactory.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

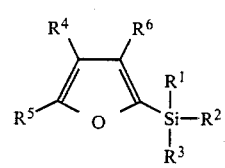

wherein
$R^1$, $R^2$ and $R^3$ are independently H, alkoxy of 1-2 carbon atoms, alkyl of 1-7 carbon atoms optionally substituted with halogen, alkenyl of 2-7 carbon atoms, phenyl or benzyl, with the proviso that the sum of the number of carbon atoms in $R^1$, $R^2$ and $R^3$ must be at least 1 and not greater than 9 with the additional proviso that no more than 2 of $R^1$, $R^2$ and $R^3$ are alkoxy;

$R^4$ and $R^5$ are independently pyridyl or

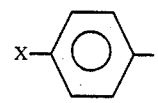

where X is H, F, Cl, Br, $R^7$, $OR^7$, $S(O)_nR^7$, $NO_2$, or

where n=0, 1 or 2; $R^7$=alkyl of 1-2 carbon atoms and $R^8$=alkyl of 1-2 carbon atoms;
with the proviso that $R^4$ and $R^5$ cannot both be

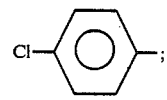

and
$R^6$ is H, or alkyl of 1-2 carbon atoms; or a pharmaceutically suitable salt thereof.

2. A compound of claim 1 wherein $R^6$ is H.

3. A compound of claim 2 wherein $R^4$ and $R^5$ are independently

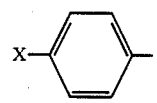

where X is H, $OR^7$, F, or $R^7$ where $R^7$ is alkyl of 1-2 carbon atoms.

4. A compound of claim 2 wherein $R^4$ and $R^5$ are independently

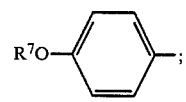

where $R^7$ is alkyl of 1-2 carbon atoms.

5. A compound of claim 2 wherein $R^4$ and $R^5$ are independently

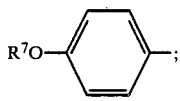

where
  $R^7$ is alkyl of 1-2 carbon atoms; and
  $R^1$, $R^2$ and $R^3$ are independently H, alkyl of 1-3 carbon atoms, or alkenyl of 2-3 carbon atoms with the proviso that the sum of the number of carbon atoms in $R^1$, $R^2$ and $R^3$ must be at least 2 and not greater than 5.

6. The compound of claim 1 which is 4,5-bis(4-methoxyphenyl)-2-trimethylsilylfuran.

7. A pharmaceutical composition consisting essentially of a suitable pharmaceutical carrier and an effective antiinflammatory or analgesic amount of at least one compound of claim 1, claim 2, claim 3, claim 4, claim 5, or claim 6.

8. A method of treating inflammation, pain or both in a mammal which comprises administering to the mammal an effective antiinflammatory or analgesic amount of at least one compound of claim 1, claim 2, claim 3, claim 4, claim 5, or claim 6.

* * * * *